(12) United States Patent
Hirsekorn

(10) Patent No.: US 8,519,202 B2
(45) Date of Patent: Aug. 27, 2013

(54) PROCESS FOR PRODUCING METHYL CHLORIDE AND SULFUR DIOXIDE

(75) Inventor: Kurt F. Hirsekorn, Midland, MI (US)

(73) Assignee: Dow Global Technologies LLC, Midland, MI (US)

(*) Notice: Subject to any disclaimer, the term of this patent is extended or adjusted under 35 U.S.C. 154(b) by 0 days.

(21) Appl. No.: 13/582,163

(22) PCT Filed: Feb. 25, 2011

(86) PCT No.: PCT/US2011/000357
§ 371 (c)(1),
(2), (4) Date: Aug. 31, 2012

(87) PCT Pub. No.: WO2011/109071
PCT Pub. Date: Sep. 9, 2011

(65) Prior Publication Data
US 2013/0006025 A1    Jan. 3, 2013

Related U.S. Application Data

(60) Provisional application No. 61/310,570, filed on Mar. 4, 2010.

(51) Int. Cl.
*C07C 17/00* (2006.01)
(52) U.S. Cl.
USPC ........................................................ 570/261
(58) Field of Classification Search
USPC ........................................................ 570/261
See application file for complete search history.

(56) References Cited

U.S. PATENT DOCUMENTS 3,256,343 A * 6/1966 McCall et al. ................ 568/639
2012/0116121 A1  5/2012 Hirsekorn et al.

OTHER PUBLICATIONS

Blum, J. et al. Desulfonylation of Aromatic Sulfonyl Halides Catalyszed by some Platinum-Metal Complexes J. Org. Chem., 1970, 35, 1895-1899.*
Miller, B. et al. The Displacement of Aromatic Substituents by Halogen Atoms J. Am. Chem. Soc. 1957, 79, 4187-4191.*
International Search Report and Written Opinion from related PCT application PCT/US2011/000357, dated Apr. 13, 2011, 8 pages.
Boeseken, et al. "The dissociation of CH3S02C1 and C2H5SO2C1 by aluminium chloride" Abstract, Recueil des Travaux Chimiques des Pays-Bas et de la Belgique (1914), 33 317-23.
Geiseler, et al. "Kinetics and Mechanism of the thermal degradation of the alkane sulfohalides, II. Mechanism of thermal degradation of alkane sulfochlorides", Zeitschrift fur Physicalische Chemie Neue Folge (1961), vol. 28, 33-50.
Van Der Heijden, et al., "Intermediates in the Destruction of Chlorinated C1 Hydrocarbons on La-Based Materials: Mechanistic Implications", Chem. Eur. J. (2007), 13, 9561-9571.
Rieche, et al. "Studies on sulfochlorides and sulfonamides—II", The Pyrolysis of sulfocholorides, Journal fur praktische Chemie, 1959, XP002631002, 19 pages.

* cited by examiner

*Primary Examiner* — Johann R Richter
*Assistant Examiner* — Medhanit Bahta
(74) *Attorney, Agent, or Firm* — Brooks, Cameron & Huebsch, PLLC

(57) ABSTRACT

Produce methyl chloride and sulfur dioxide using a reactor with lanthanum oxychloride, and contacting the lanthanum oxychloride with methanesulfonyl chloride under conditions sufficient to convert a portion of the methanesulfonyl chloride to methyl chloride and sulfur dioxide.

10 Claims, No Drawings

PROCESS FOR PRODUCING METHYL CHLORIDE AND SULFUR DIOXIDE

This application is a National Stage application under 35 U.S.C. 371 of PCT/US2011/000357, filed on Feb. 25, 2011 and published as WO2011/109071A1 on Sep. 9, 2011, which claims the benefit of U.S. Provisional Application Ser. No. 61/310,570 filed Mar. 4, 2010, the entire contents of which are incorporated herein by reference in its entirety.

This disclosure relates to a process for producing methyl chloride and sulfur dioxide from methanesulfonyl chloride.

Methyl chloride is used in production of higher hydrocarbons, methyl cellulose, quaternary ammonium salts and herbicides, and as an intermediate in production of silicone materials. Some current production processes of methyl chloride involve either methanol or methane. Additionally, methane can be employed to produce methanesulfonyl chloride as described in provisional application filing number U.S. 61-229863.

This disclosure provides a process for producing methyl chloride ($CH_3Cl$) and sulfur dioxide ($SO_2$), which comprises providing a reactor with lanthanum oxychloride (LaOCl), and contacting the lanthanum oxychloride with methanesulfonyl chloride ($CH_3SO_2Cl$) under conditions sufficient to convert a portion of the methanesulfonyl chloride to methyl chloride and sulfur dioxide.

Advantageously, selectivity for methyl chloride and/or sulfur dioxide production of the disclosed process exceeds the selectivity of processes using other catalysts at comparable temperatures.

The process conditions include a weight hourly space volume (WHSV) wherein a weight of the methanesulfonyl chloride fed to the reactor per a unit weight of the lanthanum oxychloride per hour is within a range of from 0.01 hours to 100 hours$^{-1}$. A preferred WHSV is within a range of from 0.2 hours$^{-1}$ to 1.0 hours$^{-1}$. The process conditions include a reaction temperature within a range of from 25 degrees C. (° C.) to 400° C. A preferred reaction temperature is within a range of from 250° C. to 325° C.

The process can include pretreating the lanthanum oxychloride by heating to a temperature within a range of from 250° C. to 400° C. The heating can occur in the presence of an inert gas, for example, nitrogen. The pretreating can include a promoter selected from a group consisting of chlorine ($Cl_2$), hydrogen chloride (HCl), and combinations thereof.

Lanthanum oxychloride can be converted in-situ to lanthanum trichloride via a high temperature exposure to chlorine and/or hydrogen chloride. Lanthanum trichloride is less active than lanthanum oxychloride. Thus, pretreatment including the promoter is limited such that a mixture of lanthanum oxychloride and lanthanum trichloride is formed, wherein the mixture has a chlorine atom to lanthanum atom ratio that is not greater than 1.5:1.0.

The process can include contacting the lanthanum oxychloride with a co-feed selected from the group consisting of chlorine, hydrogen chloride, oxygen ($O_2$), and combinations thereof. The methanesulfonyl chloride to co-feed molar ratio is within a range of from 1 to 100. For one or more embodiments, the co-feed is not consumed in the disclosed process.

The lanthanum oxychloride is obtainable by reacting at 22° C. lanthanum(III) chloride heptahydrate ($LaCl_3 \cdot 7H_2O$>99.9%, available from Sigma-Aldrich®) with an aqueous solution of ammonium hydroxide ($NH_4OH$, ACS reagent, 28.0%-30.0% $NH_3$ basis, available from Sigma-Aldrich®) under an argon (Ar≧99.9%, available from BOC Gases) atmosphere to provide a precipitate that is washed with water, dried, and calcined under synthetic air at 550° C. for 8 hours (hr).

The process occurs in a continuous flow reactor. Examples of the continuous flow reactor include, but are not limited to, a plug-flow reactor and a fluidized bed reactor.

EXAMPLE

(Ex) 1

Use a Hastelloy™ B reactor (25 centimeter (cm); 1.09 cm inner diameter; 1.27 cm outer diameter) to produce methyl chloride and sulfur dioxide from methanesulfonyl chloride. Load catalyst into the reactor between two 8 gram portions of quartz chips, provide nitrogen flow in a range of from 100 standard cubic centimeters per minute (sccm) to 200 sccm, pretreat the catalyst, feed methanesulfonyl chloride to the reactor (WHSV), and maintain the reactor contents at a temperature of 275° C., as shown in Table 1. Place a cylinder maintained at a temperature of 25° C. below the reaction zone of the reactor to collect non-volatile products. Feed volatile products to an online gas chromatograph. Use gas chromatography calibrations and nuclear magnetic resonance spectroscopy analysis to determine conversion and selectivity, as shown in Table 1, from the volatile and non-volatile products. Methanesulfonyl chloride conversion is calculated by two methods. First, the mass of methanesulfonyl chloride contained in the non-volatile products is compared to the mass of methanesulfonyl chloride fed to the reactor. Second, the moles of sulfur contained in the volatile products is compared to the moles of methanesulfonyl chloride fed to the reactor. The values for methanesulfonyl chloride conversion obtained by these methods are within 5% error. Methyl chloride selectivity is calculated as the moles of methyl chloride produced divided by the total moles of carbon contained in the products. Sulfur dioxide selectivity is calculated as the moles of sulfur dioxide produced divided by the total moles of sulfur contained in the products.

Ex 2-6 and Comparative Examples (CEx) A-G

Replicate Ex 1 with changes in catalyst, pretreatment, WHSV, co-feed, and/or temperature as shown in Table 1.

TABLE 1

| Ex (1-6)/ CEx (A-G) | Catalyst | Pretreatment | WHSV (hours$^{-1}$) | Co-feed | Molar ratio (Methanesulfonyl chloride to Co-feed) | Reaction Temperature (° C.) | Methanesulfonyl chloride conversion (%) | Methyl chloride selectivity (%) | Sulfur dioxide Selectivity (%) |
|---|---|---|---|---|---|---|---|---|---|
| 1 | LaOCl | Heating (250° C., 8 hr) | 0.27 | — | — | 275 | 10 | 99 | 99 |
| 2 | LaOCl | Promoter/Heating ($Cl_2$ (3 mol %)/ 400° C., 8 hr) | 0.33 | — | — | 250 | 99 | 99 | 99 |

TABLE 1-continued

| Ex (1-6)/ CEx (A-G) | Catalyst | Pretreatment | WHSV (hours$^{-1}$) | Co-feed | Molar ratio (Methanesulfonyl chloride to Co-feed) | Reaction Temperature (° C.) | Methanesulfonyl chloride conversion (%) | Methyl chloride selectivity (%) | Sulfur dioxide Selectivity (%) |
|---|---|---|---|---|---|---|---|---|---|
| 3 | LaOCl | Promoter/Heating (HCl (3 mol %)/ 400° C., 8 hr) | 0.24 | — | — | 325 | 10 | 99 | 99 |
| 4 | LaOCl | Heating (250° C., 8 hr) | 0.39 | Cl$_2$ | 2.8 | 275 | 99 | 99 | 99 |
| 5 | LaOCl | Heating (250° C., 8 hr) | 0.25 | HCl | 1.0 | 275 | 10 | 99 | 99 |
| 6 | LaOCl | Heating (250° C., 8 hr) | 0.30 | O$_2$ | 4.7 | 325 | 30 | 99 | 99 |
| A | — (quartz chips only) | Heating (250° C., 8 hr) | — | — | — | 375 | 40 | 30 | 99 |
| B | α-Al$_2$O$_3$ | Heating (250° C., 8 hr) | 0.24 | — | — | 275 | 4 | 35 | 82 |
| C | Cu/Al$_2$O$_3$ | Heating (250° C., 8 hr) | 0.30 | — | — | 250 | 90 | 41 | 99 |
| D | Nb$_2$O$_5$/SiO$_2$ | Heating (250° C., 8 hr) | 0.24 | — | — | 300 | 80 | 13 | 99 |
| E | SO$_4$/ZrO$_2$ | Heating (250° C., 8 hr) | 0.24 | — | — | 300 | 45 | 66 | 99 |
| F | LaCl$_3$ | Heating (400° C., 12 hr) | 0.07 | — | — | 275 | 3 | 99 | 99 |
| G | LaCl$_3$ | Heating (250° C., 8 hr) | 0.07 | Cl$_2$ | 1.0 | 275 | 3 | 99 | 99 |

The data summarized in Table 1 show that contacting methanesulfonyl chloride with the catalyst lanthanum oxychloride produces methyl chloride and sulfur dioxide. Additionally, selectively for methyl chloride and/or sulfur dioxide production is greater in Exs 1-6 than in CExs A-E. CExs F-G show comparable methyl chloride and sulfur dioxide selectivities to Exs 1-6, but this occurs with a three-fold reduction in methanesulfonyl chloride conversion, compared to Ex 1, even as CExs F-G have a four-fold decrease in WHSV. Additionally, Ex 2 and Ex 4 show that the Cl$_2$ co-feed increases methanesulfonyl chloride conversion as compared to Exs 1, 3, 5-6 and CExs A-G.

What is claimed is:

1. A process for producing methyl chloride and sulfur dioxide, which process comprises providing a reactor with lanthanum oxychloride, and contacting the lanthanum oxychloride with methanesulfonyl chloride under conditions sufficient to convert a portion of the methanesulfonyl chloride to methyl chloride and sulfur dioxide.

2. The process of claim 1, wherein a weight of the methanesulfonyl chloride fed to the reactor per a unit weight of the lanthanum oxychloride per hour is within a range of from 0.01 hours$^{-1}$ to 100 hours$^{-1}$.

3. The process of claim 1, wherein a weight of the methanesulfonyl chloride fed to the reactor per a unit weight of the lanthanum oxychloride per hour is within a range of from 0.2 hours$^{-1}$ to 1.0 hours$^{-1}$.

4. The process of claim 1, wherein the conditions include a reaction temperature within a range of from 25 degrees Celsius to 400 degrees Celsius.

5. The process of claim 1, wherein the conditions include a reaction temperature within a range of from 250 degrees Celsius to 325 degrees Celsius.

6. The process of claim 1, further comprising contacting the lanthanum oxychloride with a co-feed selected from the group of chlorine, hydrogen chloride, oxygen, or a combination thereof, wherein a molar ratio of methanesulfonyl chloride to the co-feed is within a range of from 1 to 100.

7. The process of claim 6, wherein the co-feed is chlorine.

8. The process of claim 1, further comprising pretreating the lanthanum oxychloride by heating the lanthanum oxychloride to a temperature within a range of from 250 degrees Celsius to 400 degrees Celsius.

9. The process of claim 8, wherein the heating of the lanthanum oxychloride occurs in the presence of a promoter selected from the group of chlorine, hydrogen chloride, or a combination thereof to form a mixture of lanthanum oxychloride and lanthanum trichloride, wherein the mixture has a chlorine atom to lanthanum atom ratio that is not greater than 1.5:1.0.

10. The process of claim 1, wherein the reactor is a continuous flow reactor.

* * * * *